United States Patent [19]
Roberts et al.
[11] Patent Number: 4,990,157
[45] Date of Patent: Feb. 5, 1991

[54] SOOTHER RETAINER

[75] Inventors: David L. Roberts, Toronto; Clyde D. Hillier, London, both of Canada

[73] Assignee: Robhill Industries Inc., Toronto, Canada

[21] Appl. No.: 435,040

[22] Filed: Nov. 13, 1989

[51] Int. Cl.[5] ........................ A61J 17/00; A61F 5/37; A61B 17/00

[52] U.S. Cl. .................................... 606/234; 606/236; 606/157; 128/846; D24/44; D24/45

[58] Field of Search ................ 128/846; 606/118, 120, 606/157, 234, 235, 236; D24/44, 45, 46

[56] References Cited

U.S. PATENT DOCUMENTS

| | | | |
|---|---|---|---|
| Re. 30,526 | 2/1981 | Hurst | 606/236 |
| D. 225,039 | 10/1972 | Sauritis | D24/46 |
| D. 295,558 | 5/1988 | Jefferson | D24/45 |
| 477,904 | 6/1892 | Lawson | 606/236 |
| D. 651,497 | 6/1900 | Ware | 606/236 |
| D. 954,066 | 4/1910 | Ware | 606/236 |
| 1,122,306 | 12/1914 | Reschke | 606/236 |
| 2,595,462 | 5/1952 | Johnson | 606/235 |
| 2,834,350 | 5/1958 | Beck | 606/236 |
| 3,247,852 | 4/1966 | Schneider | 606/120 |
| 3,455,292 | 7/1969 | Mudrinich | 606/236 |
| 3,556,104 | 1/1971 | Janklow | 606/236 |
| 3,825,012 | 7/1974 | Nicoll | 606/120 |
| 4,143,452 | 3/1979 | Hakim | 606/236 |
| 4,688,571 | 8/1987 | Tesler | 606/234 |

*Primary Examiner*—Robert A. Hafer
*Assistant Examiner*—Michael Brown

[57] ABSTRACT

A plastic retaining strap in combination with a one piece plastic clip is disclosed where the plastic clip is secured to the retaining strap in a manner to allow pivotal and sliding movement of the clip on the strap. This arrangement is particularly useful with a baby soother which is retained in a similar manner at the opposite end of the strap relative to the plastic clip. The plastic retaining strap is formed with sufficient structural integrity to move to a generally elongate configuration when external stresses are removed. The particular securement of the clip and soother accommodate the more resistant strap allowing the combination to satisfy its intended purpose, although the strap is stiffer than the flexible straps of the prior art.

12 Claims, 3 Drawing Sheets

SOOTHER RETAINER

FIELD OF THE INVENTION

The present invention relates to soother straps and in particular, soother straps of a simplified construction.

Many mothers rely on soothers or pacifiers for comforting of an infant and often have several of these ready for use. In young infants, it is important to try to maintain a relatively sterile environment and therefore, if the soother drops to the floor or other soiled surface a mother is often very reluctant to return the pacifier to the infant without first sterilizing the same. The pacifiers are generally provided with some sort of ring-like structure to allow the pacifier to be removed from the infant and in some cases people use this ring for securing of the pacifier to the child. Some mothers have used a piece of string to tie the pacifier to the child by securing of the string on the ring of the pacifier and possibly using a safety pin to attach the string to the clothes of the infant. Commercial variations of this are known where a metal clip is mechanically fastened to a strap and a further metal clasp type arrangement is provided at the opposite end of the strap for securing to a soother. This known strap is made of a cloth material and often some decorative type figure is placed near the clip which is used to fasten the strap to the infant's clothing. Although this arrangement does reduce contamination of the pacifier, the strap itself is subject to contamination and can transfer germs to the soother. Often the length of the straps are sufficient to allow wrapping of the strap around an infant's neck and the flexibility of the strap allows this to occur, threatening the safety of the infant.

There remains a need to provide a more satisfactory solution for maintaining the soother in close proximity to an infant, reducing contamination of the same while providing a securing arrangement which itself is less vulnerable to contamination and/or can easily be washed and/or sterilized. Preferably, the solution should also reduce the possibility of the strap being wound around an infant's neck.

SUMMARY OF THE INVENTION

The retaining arrangement, according to the present invention, comprises in combination a one piece plastic clip with overlapping arms at one end biased towards one another and defining a fabric engaging portion therebetween. The plastic clip further includes means for releasably engaging a strap at a position remote the fabric engaging portion. The plastic strap of the combination has at one end thereof an arrangement for releasably engaging the plastic clip. The end of the strap opposite to this includes a structure for releasably forming and maintaining a closed loop portion to allow the strap to be threaded through the ring of a soother and thereafter form a closed loop for maintaining of the soother. The components of the strap are all integral therewith, simplifying the structure and allowing convenient sterilization of the same.

BRIEF DESCRIPTION OF THE DRAWINGS

Preferred embodiments of the invention are shown in the drawings, wherein.

DETAILED DESCRIPTION OF THE PREFERRED EMBODIMENTS

Figure 1:
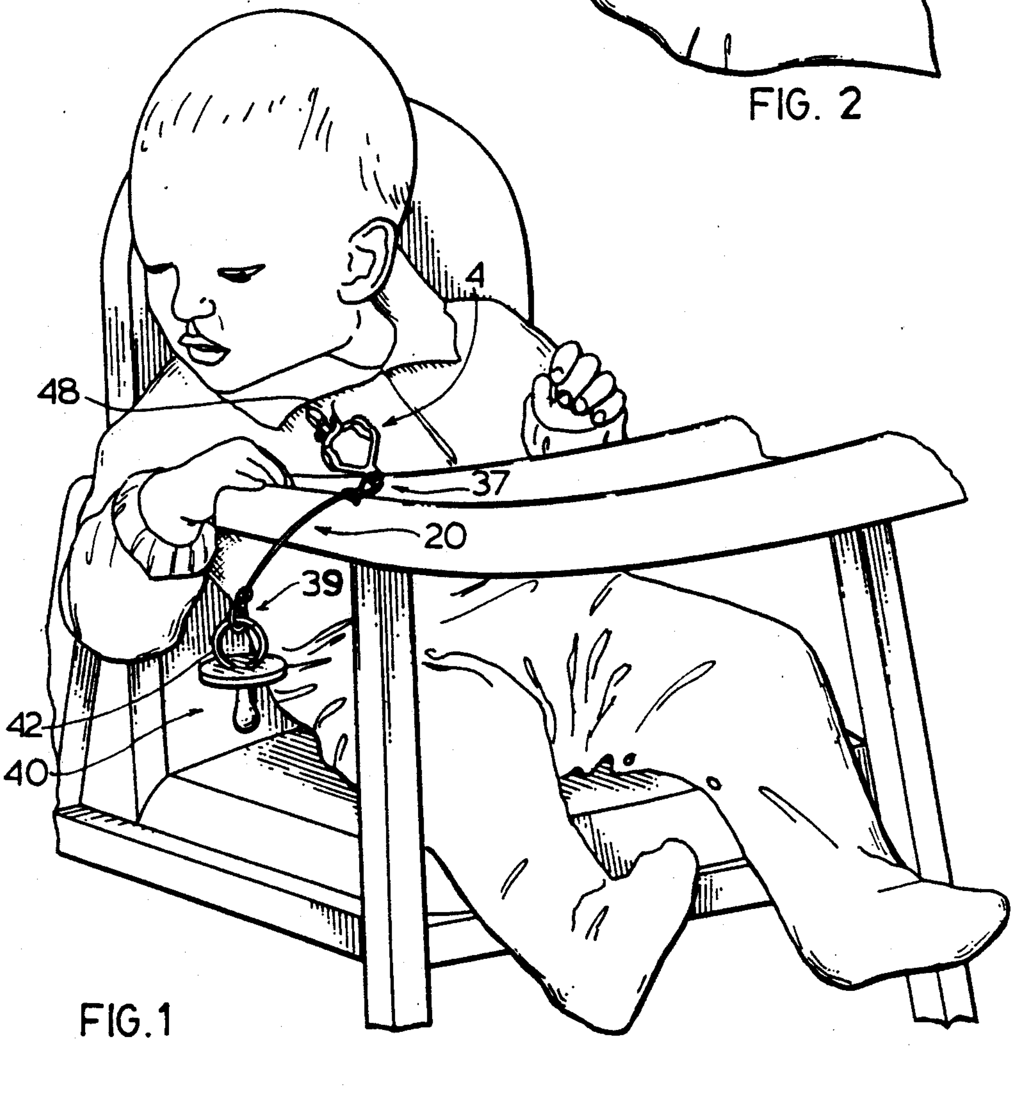
FIG. 1 is a perspective view of the retaining arrangement having a secured soother at one end attached to an infant.
Figure 3:
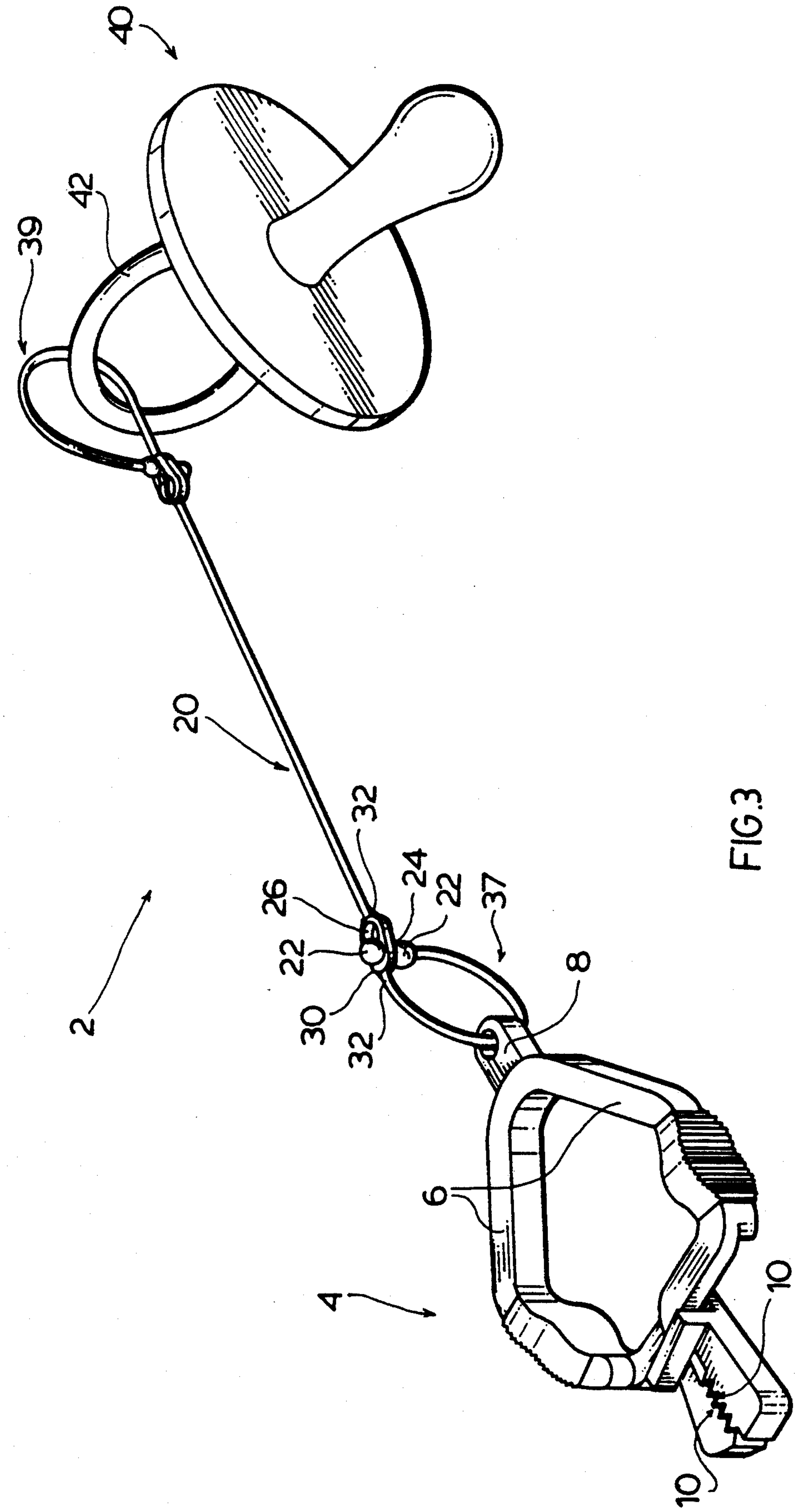
FIG. 3 is a perspective view of the retaining arrangement engaging a soother.

The retaining arrangement, generally shown as 2 in FIGS. 1 and 3, has at one end thereof a one piece plastic clip 4 which is used to secure the retaining strap to the clothing of an infant as shown in FIG. 1. The plastic clip has overlapping arms 6 biased towards one another by the stress maintained within the clip. The overlapping arms of the clip are forced past one another, creating a bias urging the arms against one another and this overlapping arrangement is maintained by the retaining bar shown as 14. If the arms both clear the bar 14, they can be then separated with the one arm passing to the outside of bar 14, rendering the clip nonoperative. The bar serves to maintain the operative relationship of the clip with the arms overlapping.

At the opposite end of the clip to the overlapping arm is an extending tab 8 having a port 9 through which the plastic strap 20 is inserted. The plastic strap 20 has at each end beads 22 separated by a narrowed portion 24 in combination with port 26 having an enlarged portion for allowing the first bead to pass through the port and a smaller retaining portion which the beads are forced into to retain the strap within the port. The port 26 is located within an enlarged flattened region 30 and this flattened region 30 is connected to the strap by means of a flared region, generally shown as 32, to avoid any high stress concentration.

The plastic strap 20 is generally circular in cross section and is resiliently deformable along its length, although it has sufficient rigidity and elasticity to return to a somewhat straight configuration if no external forces are applied. The overall length of the clip and strap is about 12 inches and the nature of the strap 20 is such that it does not like to retain a closed loop condition. As generally shown in FIG. 20, the strap remains somewhat straight or on a gentle arc and avoids any loop portions of a size for wrapping about an infant's neck, which are easily formed if a a cloth strap is used. The structural rigidity and resiliency renders the strap less likely to be wrapped about an infant's neck and the length thereof also renders this possibility less likely.

The opposite end of plastic strap 20 to the end engaging the plastic clip 4 is shown in FIG. 3 as having a closed loop formed by the beads 22 and the port 26 which engage and retain the soother 40 by means of the soother ring 42. Thus, the beads and ports for forming loops 37 and 39 provide a very simple arrangement for retaining of the clip and retaining of the soother ring while providing sufficient structural integrity to avoid a full looping of the strap about an infant's neck.

Figure 4:
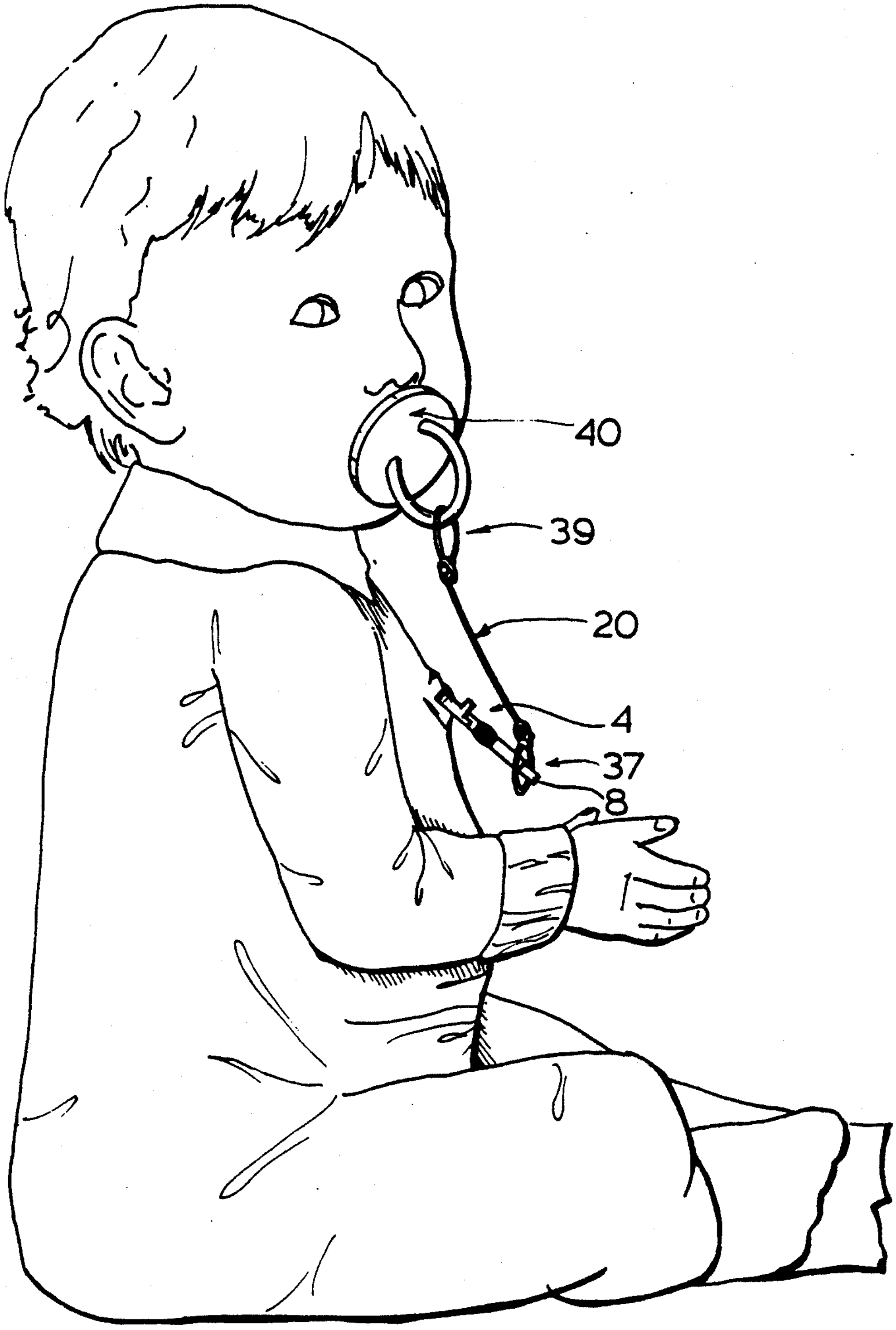
FIG. 4 is a perspective view of an infant using a soother secured by the retaining arrangement.

The generous loops at either end of the strap allow the strap to move and pivot easily relative to the soother ring and plastic clip, as shown in FIG. 4, such that the strap between the loops is subjected to less deformation and can be stronger with respect to the deformation. In FIG. 4, it can be seen that the loop attached to the plastic clip has pivotted, allowing the infant to use the soother without stressing of the strap. In some cases, the strap will be stressed, but the loops free movement will reduce the amount of stress in the arrangement during use of the strap. The strap resists, due to internal stress, forming a closed loop in its entire length, such that the possibility of wrapping the strap about an infant's neck is reduced. The strap, upon release of the external forces, returns to a generally elongate configuration.

Figure 2:
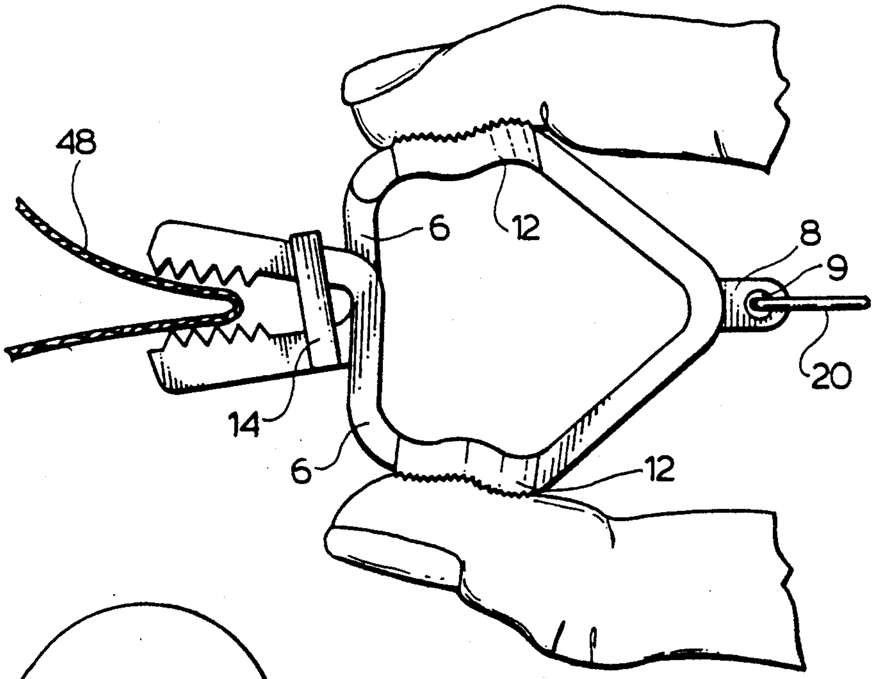
FIG. 2 is a side elevation showing details of the plastic clip.

As shown in FIG. 2, the arrangement is secured to an infant by engaging a fold of fabric, generally shown as 48 in FIG. 2, between the overlapping arm 16 and in particular, between the fabric engaging portions of the arms, generally shown as 10. A very positive engagement is achieved without damaging of the fabric. By properly placing the plastic clip 4 on the infant, the infant quickly realizes that the soother is in close proximity and will seek out the soother as required.

The one piece plastic clip 4 and the one piece plastic strap 20 of the arrangement can easily be sterilized with the soother generally shown as 40 or can be washed in a dishwasher. This avoids problems associated with contamination of fabric straps and/or the transmission of germs to the soother from the arrangement. The simplified structure of the arrangement of the present invention is thus more easily sterilized and less expensive to manufacture than the prior art, while also providing improved safety.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. In combination a baby soother, a retaining strap and a one piece plastic clip;

said baby soother including a large open ring portion to one side thereof;

said one piece plastic clip having overlapping arms biased towards one another and defining a fabric gripping portion therebetween, said plastic clip further having means for releasably engaging said strap generally remote from said fabric gripping portion;

said plastic strap at one end forming a closed loop engaging said large open ring portion of said baby soother such that said ring is slidable thereon and pivotal thereabout, said plastic strap at the opposite end forming a closed loop portion engaging said means for releasably engaging said strap such that said plastic clip is slidable along and pivotal about said respective closed loop portion, said strap having sufficient structural integrity to move to an elongate configuration when bent in the length thereof to form a loop and thereafter released.

2. In combination as claimed in claim 1 wherein said strap is about 12 inches in length.

3. A retaining arrangement comprising in combination a one piece plastic clip with overlapping arms at one end biased toward one another and defining a fabric gripping portion therebetween, said plastic clip further including means for releasably engaging a strap at a position remote from the fabric gripping portion; and a plastic strap having at one end thereof and integral with said strap means for forming and maintaining a closed loop portion which cooperates with said means for releasably engaging a strap to effect engagement of said strap and said plastic clip such that said plastic clip is freely slidable along and pivotal about said closed loop portion, the end of said strap opposite said one end including, integral therewith, means for releasably forming and maintaining a closed looped portion, and wherein said retaining strap has sufficient structural integrity to move to a generally elongate configuration when external forces are removed therefrom.

4. A retaining arrangement as claimed in claim 3, wherein said means for releasably forming and maintaining a closed loop portion includes a bead at the end of said strap and a complementary port in said strap through which said bead can be inserted and moved to a retaining position.

5. A retaining arrangement as claimed in claim 3, wherein said means for releasably forming and maintaining a closed looped portion includes two adjacent beads spaced in the length of said strap by a narrow portion of said strap, and a complementary port in said strap through which one of said beads may be inserted, said complementary port including a locking region for engaging said narrow portion of said strap and maintaining said beads either side of said port.

6. A retaining arrangement as claimed in claim 5, wherein both ends of said strap includes similar locking arrangements.

7. A retaining arrangement as claimed in claim 6, wherein said strap at said ports is flattened and enlarged to accommodate said ports while maintaining the structural integrity of the strap.

8. A retaining arrangement as claimed in claim 7 made of a plastic material which is dishwasher safe.

9. A retaining arrangement as claimed in claim 3, wherein said overlapping arms have oppositely offset abutting gripping surface.

10. A retaining arrangement as claimed in claim 9, wherein one of said overlapping arms includes, between said fabric gripping portion and said means for releasably engaging a strap, bar member positioned to retain the opposite arm in an operative position.

11. A retaining arrangement as claimed in claim 10, further including in combination a baby soother releasably retained at the end of said strap opposite said plastic clip.

12. A retaining arrangement as claimed in claim 3, wherein said retaining strap has sufficient structural integrity to resist forming a large closed loop in the length of the strap during normal use of the arrangement.

* * * * *